United States Patent [19]

Songer et al.

[11] Patent Number: 5,662,653

[45] Date of Patent: Sep. 2, 1997

[54] SURGICAL ROD-TO-BONE ATTACHMENT

[75] Inventors: Robert J. Songer, Northbrook, Ill.; Matthew N. Songer, Marquette; Francis J. Korhonen, Neqaunee, both of Mich.

[73] Assignee: Pioneer Laboratories, Inc., Marquette, Mich.

[21] Appl. No.: 603,847

[22] Filed: Feb. 22, 1996

[51] Int. Cl.⁶ ........................................ A61F 2/30
[52] U.S. Cl. ........................ 606/61; 606/72; 606/73
[58] Field of Search ........................ 606/61, 60, 73, 606/53, 72, 151, 153; 16/254, 260, 355

[56] References Cited

U.S. PATENT DOCUMENTS

| 3,651,803 | 3/1972 | Bimler | 602/16 |
|---|---|---|---|
| 4,719,905 | 1/1988 | Steffee | 606/61 |
| 4,852,213 | 8/1989 | Shewchuk | 16/260 |
| 5,075,927 | 12/1991 | Porta | 16/355 |
| 5,122,131 | 6/1992 | Tsou | 606/61 |
| 5,176,680 | 1/1993 | Vignaud et al. | |
| 5,242,445 | 9/1993 | Ashman | 606/61 |
| 5,380,323 | 1/1995 | Howland | 606/61 |
| 5,382,248 | 1/1995 | Jacobsen et al. | 606/73 |
| 5,507,746 | 4/1996 | Lin | 606/61 |
| 5,534,001 | 7/1996 | Schlapfer et al. | 606/61 |
| 5,534,002 | 7/1996 | Brumfeld et al. | 606/61 |

FOREIGN PATENT DOCUMENTS 9414385  7/1994  Sweden ........................ 606/61

OTHER PUBLICATIONS

Two pages from a brochure by the AcroMed Company entitled: Anterior ISSOLA Spinal System.
Two pages of a brochure by AcroMed Company entitled: AcroMed Special Products.

Primary Examiner—Michael Buiz
Assistant Examiner—Julian W. Woo
Attorney, Agent, or Firm—Gerstman, Ellis & McMillin, Ltd.

[57] ABSTRACT

A link for connecting surgical rods to bone comprises a bone connector such as a bone screw or a bone hook, and a head connected to one end of the bone connector. The head defines an outwardly facing first recess for receiving a portion of a surgical rod which extends transversely of the link and occupies the first recess. A cover is proportioned to fit in a position to cover the surgical rod portion occupying the first recess. A hinge member is carried by the cover and head, to permit vertical pivoting retention between the cover and the head on one side of the recess. A closure on the cover and head is provided at a position opposed to the hinge member. Specifically, the closure may comprise aligned holes, plus a set screw to provide locking closure between the cover and head with a surgical rod extending through the first recess.

18 Claims, 1 Drawing Sheet

U.S. Patent — Sep. 2, 1997 — 5,662,653
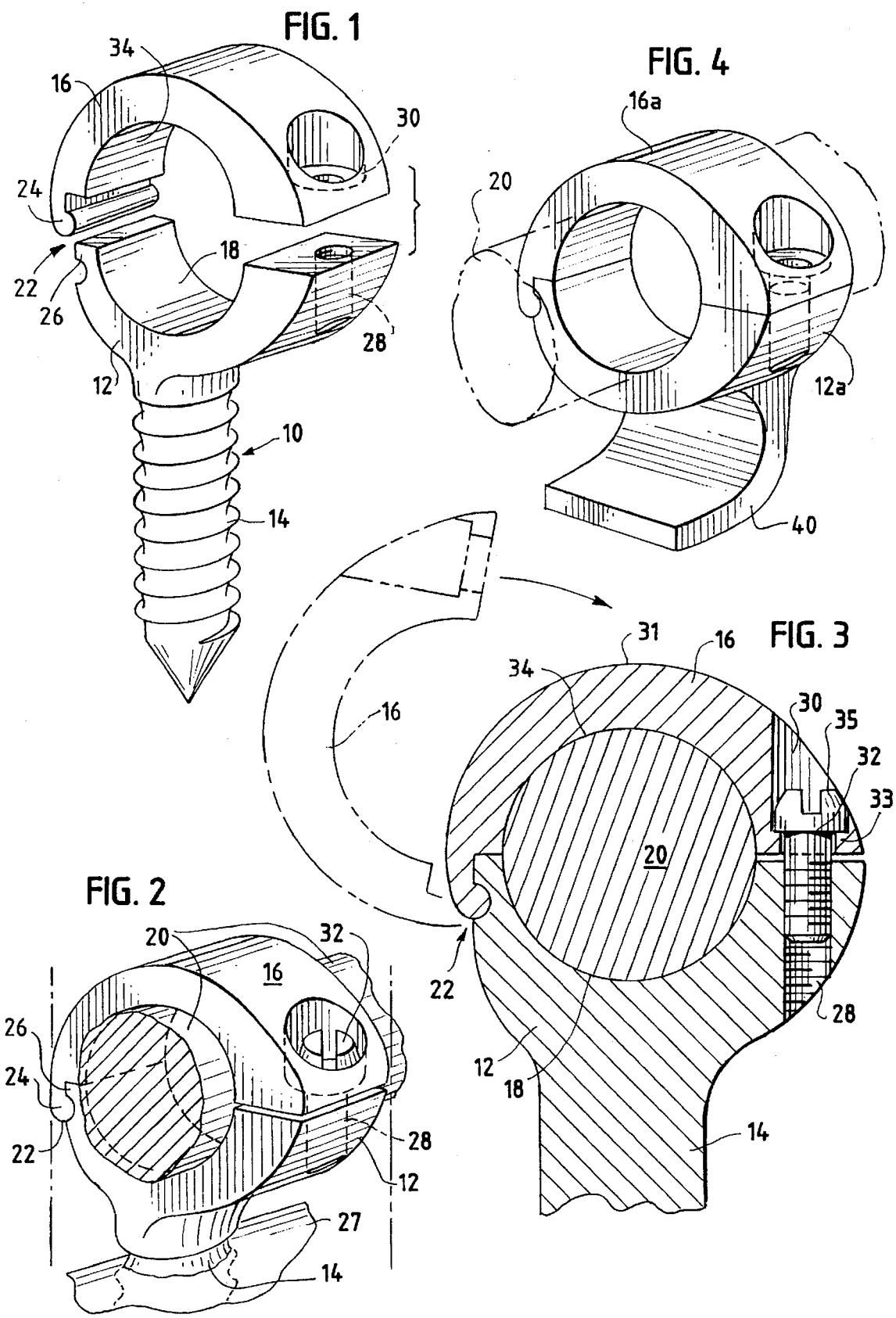

SURGICAL ROD-TO-BONE ATTACHMENT

BACKGROUND OF THE INVENTION

In the field of orthopedics, spinal rods are often implanted on at least a temporary basis to hold and support spines for various medical reasons. For example, curvature of the spine may be corrected by means of a rod, and severe fractures may be dealt with by providing support through one or more rods.

These rods are connected to the spine by means of known spinal hooks or spinal screws, for example, open screws or closed screws. Open screws define a head and a separable cap or cover to capture the rod between them onto the screws. The head itself defines a U-shape which terminates in lipped edges, being attached to the screw. Channels on the cap slide laterally onto and along the lipped edges of the U-shaped head of the screw to capture the spinal rod between them. Spinal hooks may carry heads of similar design, and are included by implication in the further discussion of the prior art.

Disadvantages exist in this construction. First, the spinal screws must be placed into various vertebra of the spine, and then the rod is placed into recesses defined by the U-shaped heads on the ends of the screws. However, typically, the spinal rods must be deeply seated into the U-shaped heads, or the cap can be applied with the lateral sliding application only with great difficulty. If the rod is not completely seated, but is spaced from the bottom of the U-recess of the spinal screw, the surgeon may find it nearly impossible to apply the cap by the lateral sliding action previously described.

Also, in the prior art spinal screws, a set screw is provided at the center of the cap. This set screw initially projects upwardly, and then is screwed to move downwardly into frictionally retentive relation with the spinal rod within the U-shaped head and the cap. It is desirable for the length of the spinal screws to be at an absolute minimum so they fit into the surgical incision without the need to enlarge the incision. The positioning of the set screw in the prior art undesirably increases the vertical profile of the spinal screws.

Also, in the conventional, open spinal screws described above, lateral retention force is provided to the rod by the set screw, forcing the rod deeply into the engagement with the walls of the U-shaped recess of the screw head. However, a substantial portion of the periphery of the rod within the screw head is not held under compressive contact by either the set screw or the recess walls. Thus, the possibility of frictional slippage of the spinal rod is substantial with respect to conventional spinal screws.

Another type of spinal screw is the closed screw, where the screw head carries a preformed aperture without a removable cap. A set screw, coaxial with the bone screw, then presses the rod within the aperture of the screw head against an opposed aperture wall for retention of the rod.

Closed screws exhibit some disadvantages similar to the open screws. Also, it is of course impossible to apply a spinal rod laterally into engagement with a closed spinal screw. The end of the spinal rod must be threaded through the preformed aperture, and, in many surgical situations, that is not possible.

The prior art also utilizes links for connecting surgical rods to bone in which a hook rather than a screw is used. Apart from that, a head is provided with an aperture which may be a preformed aperture, or may have a cap of the type described above.

Another type of bone screw is disclosed in Vignaud et al. U.S. Pat. No. 5,176,680.

In accordance with this invention, a link is provided for connecting surgical rods to bone, in which the above disadvantages are effectively eliminated, providing substantially improved ease of installation during the surgical process, coupled with improved retentive characteristics shown by the links of this invention for connecting the surgical rods to bone.

DESCRIPTION OF THE INVENTION

In accordance with this invention, a link is provided for connecting surgical rods to bone, which link comprises a bone connector such as a screw. A hook may also be used as the bone connector, in which the hook extends around behind the bone, and is retained there by a degree of retention force generally provided by the rod to which the link connects.

A head is connected to one end of the bone connector. The head defines an outwardly facing first recess for receiving a portion of a surgical rod.

A cover or cap is provided, being proportioned to fit on the head in a position to cover a surgical rod portion that occupies the first recess.

In one aspect of this invention, a hinge member is carried by the cover and head to permit vertical pivoting retention (assuming that the longitudinal axis of the link is vertical) between said cover and head, the hinge being positioned on one side of the first recess. A closure on the cover and head is provided at a position opposed to the hinge member to lock the cover and head together. Thus, the rod may be placed in the first recess, and the cover or cap brought vertically downward onto the rod by vertical pivoting action from the hinge as the cover is closed into retained relation on the head of the link. In so doing, the cover can press downwardly on the rod portion positioned in the first recess, more easily forcing the rod downwardly into fully seated relation with the recess.

Thus, the cover is more easily closed and locked into position. Corresponding covers or caps of prior art bone screws must slide laterally along a track into their closed relation, possibly fighting a portion of surgical rod occupying the recess all the way, if the surgical rod is not well seated in the screw head. This is often the case in actual surgical experience, since it is difficult to perfectly align the various prior art bone screws in the patient so that the surgical rod is naturally well seated in all of them.

The closure of the link of this invention may comprise aligned holes in each of the cover and head on a side opposed to the hinge member, to receive a screw of other connecting member to provide locking closure between the cover and head, with a surgical rod extending through the recess.

The hinge member used in this invention may be a permanently connected hinge, or a hinge with separable components. It may preferably comprise a hook member carried by each of the head and cover. The hook members may then be separably engaged by the surgeon to define and form the hinge member, which then may be closed to lock the surgical rod in place. By such a technique, a smaller surgical incision may be possible, since there is no need to place the cover in a completely lateral position beside the head to slide it into locked position. Instead, one can simply engage the respective hooks of the head and cover at about a 45 degree angle or so, and then pivot the cover by the resulting hinge into the closed relationship. Also, the head and cover can laterally slide together into position in parallel relation if that is appropriate.

Preferably, the cover may define a second recess which is proportioned to form a substantially cylindrical space with the first recess, when the cover occupies the position covering the first recess. Typically, both the first and second recesses may be substantially semi-cylindrical. Also, it is preferred for the first and second recesses to be sized so that the specific surgical rod used to occupy the recesses is held with compression about substantially the entire outer surface of the surgical rod portion which is within the first and second recesses. Thus, a larger area of the outer surface of the surgical rod is in frictionally retainer contact with the walls of the first and second recess and also the set screw, approximating 360 degree retention of the surgical rod. Accordingly, the force retired to cause either longitudinal or rotational slippage of the surgical rod in the link of this invention can be higher than the corresponding slippage force of the prior art links, where substantially less than 360 degree retention of the surgical rod is provided.

As an important feature of the invention, the cap or cover comes down upon the surgical rod occupying the first recess in a longitudinal (vertical) manner, i.e., more or less parallel to the axis of the screw when screw threaded links of this invention are used, and in a corresponding direction when a link having a bone hook or another bone connector is used. This vertical application of the cover to the head of the link can force incompletely seated rods into complete seating. This can be done with much greater ease on the part of a surgeon, when compared with the closing motion of the prior art in which a spinal screw cap laterally slides along a pair of U-shaped prongs of the head, since the incompletely seated spinal rod will seriously interfere with the sliding action. However, preferred embodiments of the connecting links of this invention can still have their caps or covers also applied from a lateral rather than a vertical direction, if the surgeon desires to do that for any reason.

DESCRIPTION OF THE DRAWINGS

FIG. 1 is a perspective view of a spinal screw in accordance with this invention;

FIG. 2 is an enlarged, fragmentary, perspective view of the head and cover of the spinal screw of FIG. 1;

FIG. 3 is a fragmentary, elevational view of the spinal screw of FIG. 2, showing the cover in open, hinged relation with the head; and FIG. 4 is a perspective view of a spinal hook which makes use of the present invention.

DESCRIPTION OF SPECIFIC EMBODIMENTS

Referring to FIGS. 1–3, a spinal screw 10 is shown having a U-shaped head 12, a bone-connecting, screw-threaded shank 14, and a cover 16. Head 12 defines an outwardly facing, semi-cylindrical first recess 18 for receiving a portion of surgical rod 20. Cover 16 is proportioned to fit in a position to cover the portion of the surgical rod 20 which occupies first recess 18, as shown in FIG. 2.

To accomplish this, a separable hinge member 22 is provided between head 12 and cover 16 at one side of recess 18. Hinge member 22, in this embodiment, defines a separable hinge comprising a first hook member 24 carried by cover 16 and extending substantially the length of cover 16 (parallel to the axis of recess 18 and spinal rod 20 and perpendicular to screw shank 14). A second hook member 26 is defined by head 12, with hook 26 also extending substantially the length of head 12, parallel to hook member 24. As shown in FIG. 2, the respective hooks 24, 26 interlock with each other to provide hinged retention when cover 16 is in or approaching closed position over head 12, and for a range of pivoting positions, so that cover 16 can be swung open or closed in hinged manner, as illustrated by FIG. 3. Nevertheless, cover 16 can be separated from head 12 as the bone screw 10 is being advanced into a bone 27 or the like. Then cover 16 can be added to the system by connecting the respective hooks 24, 26 and closing the cover to the configuration of FIG. 2.

Thus, cover 16 can be applied substantially vertically to the screw and head, the term "vertically", referring to the axial direction of the screw 14. However, if desired, cover 16 can be applied from horizontal directions as well, so that the link of this invention is easily assembled while placed deep in a surgical incision, after the screw 14 has been inserted into a bone.

Head 12 defines a threaded hole 28 on a side of the recess 18, which is on a side of head 12 opposed to hinge 22, spaced from recess 18. Cover 16 defines an unthreaded hole 30, which is positioned to engage hole 28 when the cover 16 is in the desired, closed position as shown in FIG. 2, covering surgical rod 20. A set screw 32 may be initially carried in hole 30, being blocked from falling through hole 30 by annular shoulder 33 (FIG. 3) of hole 30 that engages head 35 of the set screw. Set screw 30 may then advanced into threaded hole 28 to lock cover 16 into the position of FIG. 2.

As a further advantage, it can be seen that set screw 30 is laterally positioned from outermost end 31 of link 10, and thus is longitudinally spaced from that end also because of the convex shape of the top of cover 16. Set screw 30 thus is spaced from both ends of the link of this invention so that the vertical profile of the link can be reduced. In some links of the prior art, a set screw occupies a central, endmost position on the cover or cap of the link, being in coaxial relation with the screw. Here, the set screw is laterally displaced, and also spaced from the end 31 of the link connector of this invention.

Cover 16 also defines a second recess 34, which may be of substantially semi-cylindrical shape. As shown in FIG. 3, the first recess 18 and second recess 34 are brought together to form a substantially cylindrical space together with each other in the closed relationship between the cover and head. It is preferred for the dimensions of surgical rod 20 (which is typically a spinal rod) and recesses 18, 34 to be proportioned so that surgical rod 20 is held in the recesses 18, 34 with compression about most or all of the entire outer rod surface within the recesses. Because of this, a larger surface area of frictional retention is provided than in prior art bone-rod links, so that less slippage of the spinal rod either longitudinally or rotationally takes place in this present invention.

Also, as cover 16 is pivoted into its closed relationship with head 12 as shown in FIG. 3, a substantial downward pressure can be easily exerted on spinal rod 20 to fully seat it into recess 18. This can be easily accomplished. Cover 16 is pulled into place by advancing set screw 32, even if there is some resistance provided by the spinal rod to closure. To the contrary, in many situations of the prior art where horizontal sliding of the head into locked position is required, the locking of the head into place can be a difficult proposition if the spinal rod 20 is not fully seated.

Referring to FIG. 4, another embodiment of this invention is shown, specifically a spinal hook 40 which carries a head 12a which may be of a design similar to head 12 of the previous embodiment. A cover 16a may be placed on head 12a, with cover 16a being identical in design to cover 16, so that the advantages of this invention can be achieved with a spinal hook as well as a spinal screw or, for that matter, with any design of bone connector for retaining a head on a bone to receive and hold a rod.

Recesses 18, 34 may be off center in head 12, 12a and cover 16, 16a to provide room for set screw 32 and the holes 28, 30.

Accordingly, by this invention a link is provided for connecting surgical rods to bone, in which the attachable cover may be applied with significant advantages over the prior art surgical rods. Specifically, the substantially axial (vertical) direction of application of the cover provides significant advantages as described above, and may be a valuable feature, particularly since the cover is being applied to the head in the highly constrained environment of a surgical incision. However, if desired, the cover can be applied laterally if desired in the manner of some prior art bone screws, if circumstances dictate the need for that, but with much greater ease.

The above has been offered for illustrative purposes only, and is not intended to limit the scope of the invention of this application, which is as defined in the claims below.

That which is claimed is:

1. A link for connecting surgical rods to bone, which comprises: a bone connector and a head formed as one piece said head defining an outwardly facing first recess for receiving a portion of a surgical rod; a cover, proportioned to fit in a position to oppose and to cover said first recess; a hinge member carried by said cover and head to permit retention between said cover and said head on one side of said recess; said cover defining a second recess proportioned to form a substantially cylindrical space with the first recess, with the cover occupying said position, said first and second recesses receiving a surgical rod in said recesses and exclusively holding said rod with a substantially uniform area of compressive contact about substantially the entire outer rod surface within said first and second recesses; and a closure on the cover and head at a position opposed to said hinge member.

2. The link of claim 1 in which said closure defines aligned holes on a side of said cover and head opposed to said hinge member, and a screw to provide locking closure in said holes between said cover and head with a surgical rod extending through said recess.

3. The link of claim 2 in which a set screw occupies the hole of at least said cover, said set screw being positioned to be advanced into the hole of said head which is threaded, while a portion of said set screw remains in the cover, said set screw and holes being spaced from the ends of said link and the longitudinal axis of said link and laterally spaced from the recess.

4. The link of claim 1 in which said hinge member comprises a hook member carried by each of said head and cover, said hook members separately engaging each other to form said hinge member, whereby said cover is separable from said head.

5. The link of claim 1 in which said bone connector comprises a bone screw.

6. The link of claim 1 in which said bone connector comprises a retention hook.

7. A link for connecting surgical rods to bone which comprises: a bone connector and a head formed as one piece said head defining an outwardly facing first recess receiving a portion of a surgical rod; a cover proportioned to fit in a position to oppose and to cover said surgical rod portion occupying said first recess; a hinge member carried by said cover and head to permit pivoting retention between said cover and head on one side of said recess, said cover and head defining aligned holes on a side of said cover and head opposed to said hinge member and laterally spaced from said recess, and a screw to provide locking closure in said holes between said cover and head; said cover defining a second recess proportioned to form a substantially cylindrical space with the first recess when the cover occupies said position, said surgical rod occupying said first and second recesses, said rod being exclusively held by said link with a substantially uniform area of compressive contact within said recesses about substantially the entire outer rod surface within said first and second recesses.

8. The link of claim 7 in which a set screw occupies the hole of at least said cover, said set screw being positioned to be advanced into the hole of said head which is threaded, while a portion thereof remains in the cover, said set screw being spaced from the ends of said link and the longitudinal axis of said link.

9. The link of claim 8 in which said hinge member comprises a hook member carried by each of said head and cover, said hook members separably engaging each other to form said hinge member.

10. The link of claim 9 in which said bone connector comprises a bone screw.

11. The link of claim 9 in which said bone connector comprises a retention hook.

12. The method of connecting surgical rods to bone, which comprises attaching to a bone connector of a link formed with a head as one piece placing a surgical spinal rod, positioned generally parallel to the spine of a patient, into an outwardly facing first recess of said head; pivoting a cover connecting to a said head by a hinge member into closing engagement with said head with the surgical rod enclosed between said cover and head, while urging by said closing cover said surgical rod into fully seated relation with said first recess by the pivoting action of said cover as said cover closes upon said head; and locking said cover and head into closed relation.

13. The method of claim 12 in which said cover and head are locked together at a side thereof opposed to the hinge member by placement of a screw into aligned holes respectively carried by said cover and head for screw threaded locking of the cover and head together.

14. The method of claim 12 in which said cover defines a second recess which is occupied by a portion of said rod when the cover and head are locked together, said first and second recesses respectively forming a substantially cylindrical space defining walls which exclusively hold said rod with compressive contact about substantially the entire outer rod surface within said first and second recesses.

15. Th method of claim 14 in which said hinge member comprises a hook member carried by each of said head and cover, said hook members separably engaging each other to form a separable hinge member.

16. The method of claim 12 in which said hinge member comprises a hook member carried by each of said head and cover, said hook members separably engaging each other to form a separable hinge member.

17. A link for connecting surgical rods to bone, which comprises: a bone connector and a head formed as one piece said head defining an outwardly facing first recess for receiving a portion of a surgical rod; a cover proportioned to be attached to said head in a position to cover said first recess; a hinge member carried by said cover and head to permit vertical pivoting relation between said cover and head on one side of said recess; said hinge member comprising a hook member carried by each of said head and cover, said hook members separably engaging each other to form said hinge member, whereby said cover is separable from said head; and a closure on the cover and head at a position opposed said hinge member.

18. The link of claim 17 in which the cover defines an outer end of generally convex shape and a second recess proportioned to form a substantially cylindrical space with the first recess when the cover occupies said position, said first and second recesses receiving a surgical rod and said recesses being proportioned for holding said rod with compressive contact about substantially the entire rod surface.

\* \* \* \* \*